United States Patent [19]

Baldwin

[11] Patent Number: 4,474,781

[45] Date of Patent: Oct. 2, 1984

[54] TREATING HYPERTENSION WITH AMINOALKOXYPYRIDINES

[75] Inventor: John J. Baldwin, Lansdale, Pa.

[73] Assignee: Merck & Co., Inc., Rahway, N.J.

[21] Appl. No.: 132,244

[22] Filed: Mar. 20, 1980

Related U.S. Application Data

[62] Division of Ser. No. 25,826, Apr. 2, 1979, Pat. No. 4,259,327.

[51] Int. Cl.$^3$ .................. A61K 31/535; A61K 31/44
[52] U.S. Cl. .............................. 424/248.57; 424/250; 424/263; 424/267; 544/124; 544/360; 546/193; 546/300
[58] Field of Search ............... 544/124, 360; 546/193, 546/300; 424/248.57, 250, 263, 267

[56] References Cited

U.S. PATENT DOCUMENTS 3,370,059  2/1968  Schuler et al. ................. 544/124
4,206,117  1/1980  Von Philipsborn et al. ....... 424/246

FOREIGN PATENT DOCUMENTS 1445649  1/1969  Fed. Rep. of Germany ...... 546/300

Primary Examiner—Robert W. Ramsuer
Attorney, Agent, or Firm—Daniel T. Szura; Harry E. Westlake, Jr.

[57] ABSTRACT

Substituted aminoalkoxypyridines of the formula

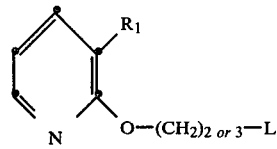

where $R_1$ is CN or $CF_3$ and L is dialkylamino or six-membered N heterocycle are disclosed. The compounds are useful as antihypertensive agents.

8 Claims, No Drawings

TREATING HYPERTENSION WITH AMINOALKOXYPYRIDINES

This is a division of application Ser. No. 25,826, filed Apr. 2, 1979, now U.S. Pat. No. 4,259,327.

BACKGROUND OF THE INVENTION

The present invention concerns certain substituted aminoalkoxypyridines which have useful pharmacological activity e.g. as antihypertensive agents.

A new class of substituted pyridines having pharmaceutical activity have been discovered.

SUMMARY OF THE INVENTION

Compounds of the formula

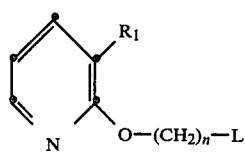

where $R_1$ is CN or $CF_3$ and L is a dialkylamino or six membered N-heterocyclic group and use as pharmaceutical agents.

DESCRIPTION OF THE PREFERRED EMBODIMENTS

An embodiment of the present invention is compounds of the formula

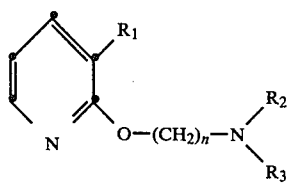

and pharmaceutically acceptable salts thereof wherein
n is 2 or 3,
$R_1$ is —CN or —$CF_3$, and
$R_2$ and $R_3$ when separate, are $C_1$-$C_6$alkyl and when joined with N form a heterocyclic piperidinyl, piperazinyl, N—$C_1$-$C_4$alkylpiperazinyl or morpholino group.

$R_1$ maybe CN or $CF_3$ and preferably CN. $R_2$ and $R_3$ are $C_1$-$C_6$alkyl e.g. methyl, isopropyl or n-hexyl, with $C_1$-$C_3$alkyl being preferred and $CH_3$ most preferred The

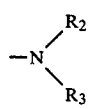

heterocyclic group is

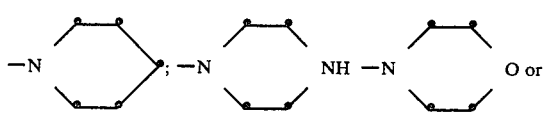

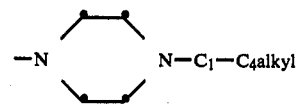

e.g. $CH_3$, t-butyl, ethyl and the like.

Pharmaceutically acceptable salts include salts of the formula I compounds with appropriate inorganic and organic acids. Suitable inorganic acids are sulfuric acid, phosphoric acid the hydrogen halides such as HCl, HI, HBr, and the like. Suitable organic acids include carboxylic acids such as acetic acid, oxalic acid, maleic acid, fumaric acid, pamoic acid, pivalic acid, succinic acid, tartaric acid, propionic acid and the like as well as non-carboxylic acid such as isethionic acid and the like. Preferred salts are those with the hydrogen halides especially HCl, maleic acid, pivalic acid and isethionic acid.

One class of preferred compounds are those having the formula

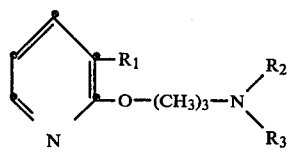

More preferred compounds of formula II are those where

(a) is —$N(C_1$-$C_4$alkyl$)_2$ especially —$N(CH_3)_2$ or (b) N-methylpiperazinyl, piperidinyl or morpholino and especially morpholino. $R_1$ is more preferably CN.

Another class of preferred compounds have the formula

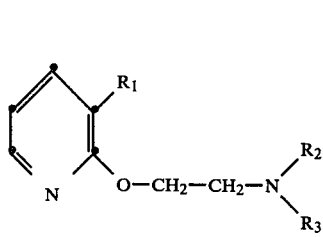

More preferred III compounds are those where —$NR_2R_3$ is (a)—$N(C_1$-$C_4$alkyl$)_2$ especially —$N(CH_3)_2$ and (b) morpholino, piperidinyl or N—$C_1$-$C_4$alkyl preferably N—$CH_3$ piperazinyl and especially morpholino. $R_1$ is most preferably CN.

The compounds of the present invention have useful pharmaceutical activity as antihypertensives and vasodilators.

These activities were determined by testing representative compounds in appropriate animal models. The antihypertensive activity was determined in spontaneously hypertensive (SH) rats. The vasodilation activity was determined in dogs.

The antihypertensive activity in SH rats indicates that the compounds are useful in treating hypertension in humans. In treating hypertension in humans, the compound of the present invention can be administered by any suitable route e.g. orally, parenterally, intravenously and the like, in a suitable dosage form. Thus, for oral administration the compounds may be administered as tablets, troches, capsules, encapsulated, in liquid form such as solutions, emulsions, suspensions and the like. For parenteral or intravenous administration suitable dosage forms are solutions, emulsions and the like.

The dosage forms which are used are prepared using conventional procedures and may contain suitable compounding ingredients that is diluents, or carriers, including emulsifying agents, flavorings, sweetening agents, thickening agents and the like. The pharmaceutical compositions containing the compounds of the present invention constitute another embodiment of the present invention.

The daily human dosage of the present compounds may be varied. It can range from about 50 to about 3000 mg., preferably from about 100 to about 2000 mg. and more preferably from about 100 to about 1000 mg.

The compounds of the present invention may be prepared by any convenient process. One such process is illustrated by the following equation

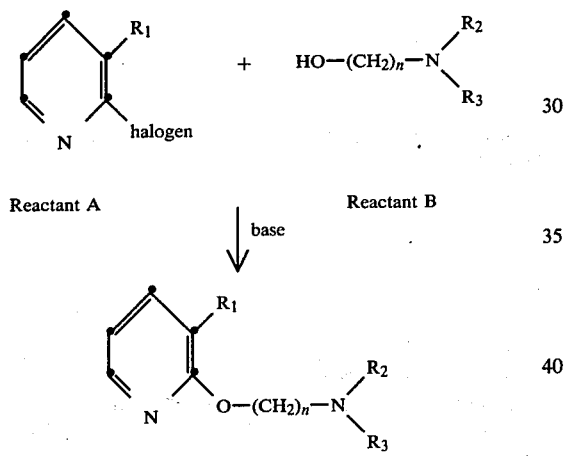

Halogen may be Cl, Br or F, with Cl being preferred.

The reaction is ordinarily carried out in a suitable solvent such as dimethylformamide (DMF).

Any suitable base such as NaH, K-O-t-butyl and the like may be used. The reaction is conveniently carried out at room temperature and atmospheric pressure although higher temperatures and pressures may be used.

The pharmaceutical acid salt of the formula I compound is obtained by treating the free base with an appropriate acid or anhydride using conventional reaction conditions and solvents.

The following examples illustrate the preparation of compounds of formula I. The temperatures are in degrees Celsius.

EXAMPLE 1

2-(2-Dimethylaminoethoxy)-3-cyanopyridine hydrochloride (XI)

To 2-dimethylaminoethanol (1.3 g, o., 015 m) in DMF (25 mL) was added 57% NaH in mineral oil (0.63 g, 0.015 m). After stirring 0.5 hours at 25° C., a solution of 2-chloro-3-cyanopyridine (2 g, 0.015 m) in DMF (10 mL) was added. The reaction mixture was stirred 20 hours, concentrated to 10 mL and added to $H_2O$ (25 mL). The solution was extracted with $CHCl_3$; the organic layer was dried, filtered and concentrated. The resulting oil was dissolved in $Et_2O$ and treated with HCl in MeOH to yield after recrystallization from $Et_2O$-iso-PrOH 0.8 g (23%) of (XI) m.p. 148°–150° C.

EXAMPLE 2

2-(2-Morpholinoethoxy)-3-cyanopyridine HCl 2-(2-Morpholinoethoxy)-3-cyanopyridine was made by essentially the same procedure as Example 1 using an appropriate amount of N-(2-hydroxyethyl)morpholine in place of 2-dimethylaminoethanol. The m.p. of the 2-(2-morpholinoethoxy)-3-cyanopyridine hydrochloride salt was 204°–206.5°.

The following table lists reactants and products obtained using the procedure substantially as described in Example 1.

| Example | Reactant A | Reactant B | Product |
|---|---|---|---|
| 3 | (pyridine with $CF_3$, Cl) | $HO-(CH_3)_2-N(C_6H_{13})_2$ | (pyridine with $CF_3$, $O-(CH_2)_2-N(C_6H_3)_2$) |
| 4 | (pyridine with $CF_3$, Br) | $HO-(CH_2)_2-N$ \_/ $N-CH_3$ | (pyridine with $CF_3$, $O-(CH_2)_2-N$ \_/ $NC_2H_3$) |

| Example | Reactant A | Reactant B | Product |
|---|---|---|---|
| 5 | pyridine with CN and Cl | $HO-(CH_2)_3-N(C_4H_9)_2$ | pyridine with CN and $O-(CH_2)_3-N(C_4H_9)_2$ |
| 6 | pyridine with CN and Br | $HO-(CH_2)_3-N$(piperidine) | pyridine with CN and $O-(CH_2)_3-N$(piperidine) |
| 7 | pyridine with $CF_3$ and F | $HO-(CH_2)_2-N$(morpholine) | pyridine with $CF_3$ and $O-(CH_2)_2-N$(morpholine) |

Claims to the invention follow.

What is claimed is:

1. A method of treating hypertension in humans which comprises administration of an antihypertensive amount of a compound having the formula

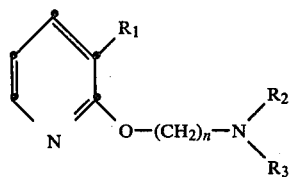

and pharmaceutically acceptable salts thereof wherein
n is 2 or 3,
$R_1$ is $-CF_3$, and
$R_2$ and $R_3$ when separate, are $C_1-C_6$alkyl and when joined with N form a heterocyclic piperidinyl, piperazinyl, N—$C_1-C_4$alkylpiperazinyl or morpholino group.

2. The method of claim 1 wherein n is 3 and said $R_2/R_3$alkyl is $C_1-C_4$alkyl.

3. The method of claim 2 wherein $R_2$ and $R_3$ are separate and are $CH_3$.

4. The method of claim 2 wherein $R_2$ and $R_3$ are joined.

5. The method of claim 1 wherein n is 2 and said $R_2/R_3$alkyl is $C_1-C_4$alkyl.

6. The method of claim 5 wherein $R_2$ and $R_3$ are separate and are $CH_3$.

7. The method of claim 5 wherein $R_2$ and $R_3$ are said heterocyclic group.

8. The method of claim 7 wherein said heterocyclic group is morpholino.

* * * * *